United States Patent [19]

Samuel

[11] Patent Number: 5,189,690
[45] Date of Patent: Feb. 23, 1993

[54] FLUOROSCOPY ORIENTATION DEVICE

[76] Inventor: Ronald Samuel, 46 Township Line Rd. Apt. 301, Elkins Park, Pa. 19117

[21] Appl. No.: 757,036

[22] Filed: Sep. 9, 1991

[51] Int. Cl.⁵ ............................................. H05G 1/28
[52] U.S. Cl. .................................. 378/162; 378/163; 378/164; 378/205
[58] Field of Search ............... 378/162, 163, 164, 165, 378/204, 205, 190, 170, 62, 20

[56] References Cited

U.S. PATENT DOCUMENTS

| | | |
|---|---|---|
| 2,579,186 | 12/1951 | Haboush . |
| 4,061,924 | 12/1977 | Jacoby et al. . |
| 4,274,006 | 6/1981 | Caine . |
| 4,722,336 | 2/1988 | Kim et al. . |
| 4,750,487 | 6/1988 | Zanetti . |
| 4,953,193 | 8/1990 | Robinson ............................. 378/162 |
| 5,031,203 | 7/1991 | Trecha ................................. 378/205 |

Primary Examiner—David P. Porta
Attorney, Agent, or Firm—Ferrill, Logan, Johns & Blasko

[57] ABSTRACT

A device for assisting a fluoroscope operator in orienting a fluoroscope on an object during a fluoroscope examination, and thereby reduce the time of use and exposure to radiation, which device consists of a sheet transparent to x-ray radiation, preferably disc shaped, possessing orientation indication means, such as radiopaque symbols, numbers and letters which may be combined in any combination. The orientation device is mounted on the fluoroscope's receiver, thereby positioning the sheet and orientation indicators between the receiver tube and the object being examined. The orientation indicators are visible on the fluoroscope's monitor, clearly indicating direction and providing guidance for the fluoroscope operator during the examination.

20 Claims, 5 Drawing Sheets

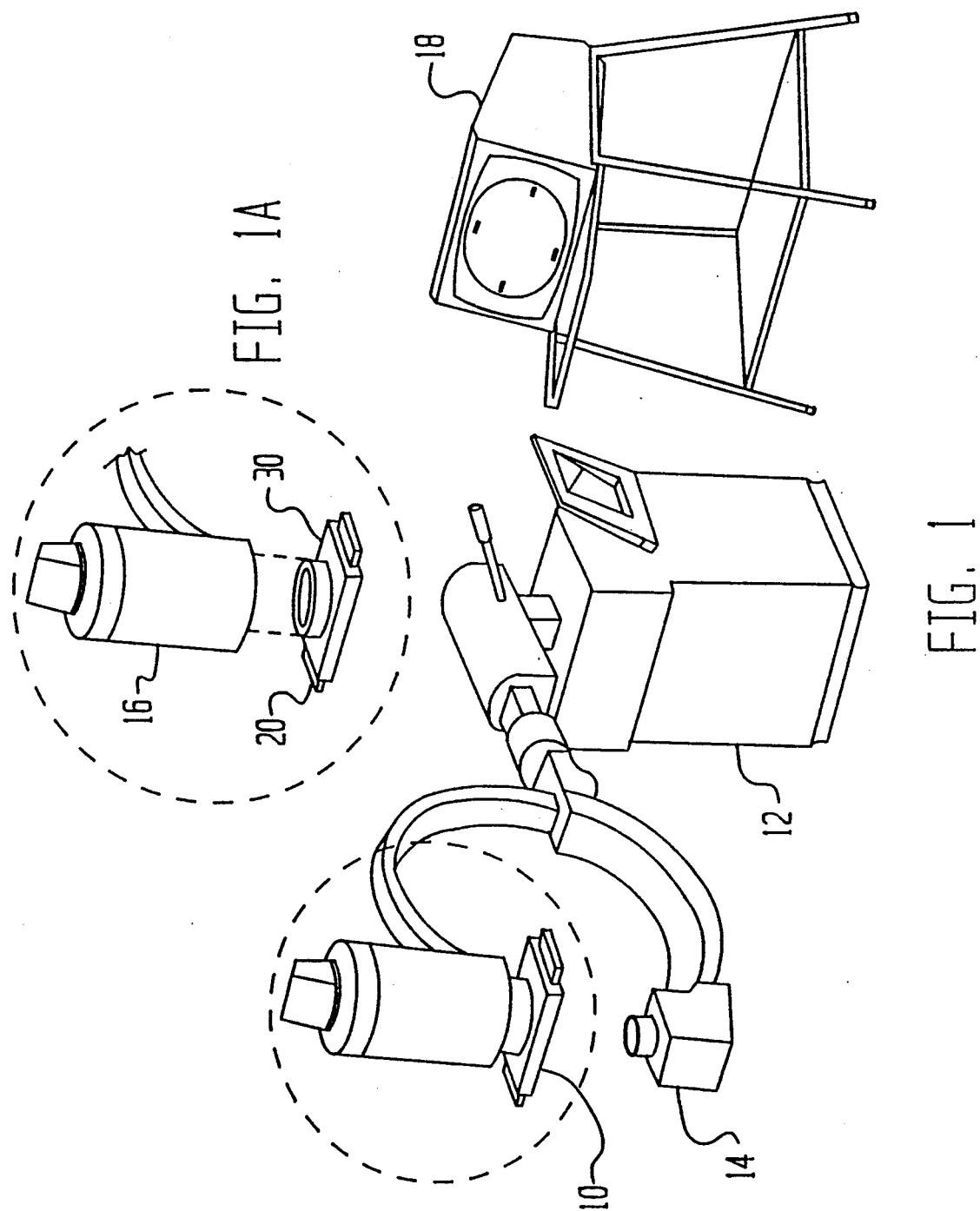

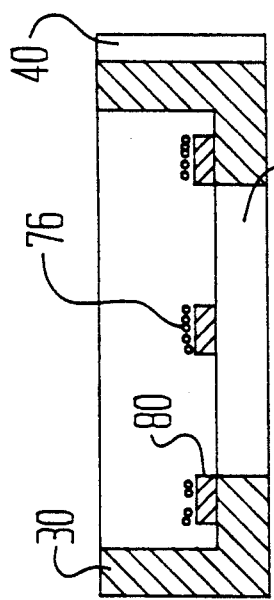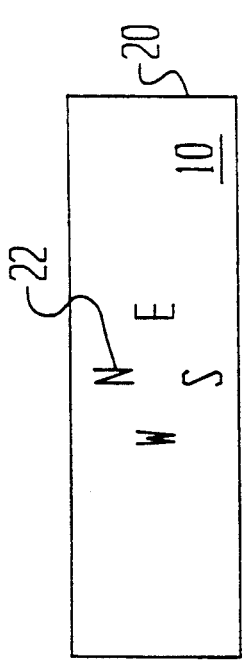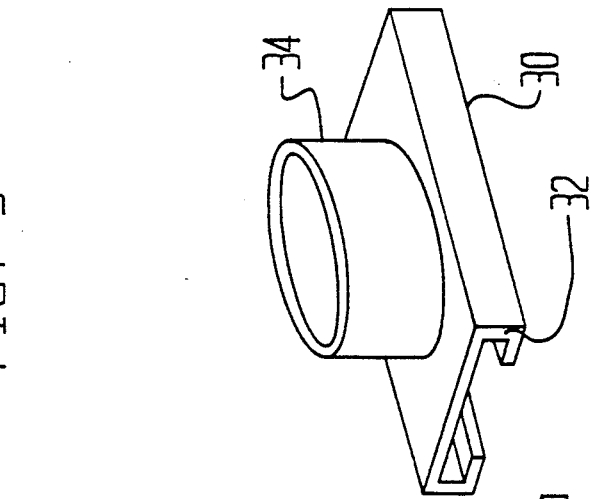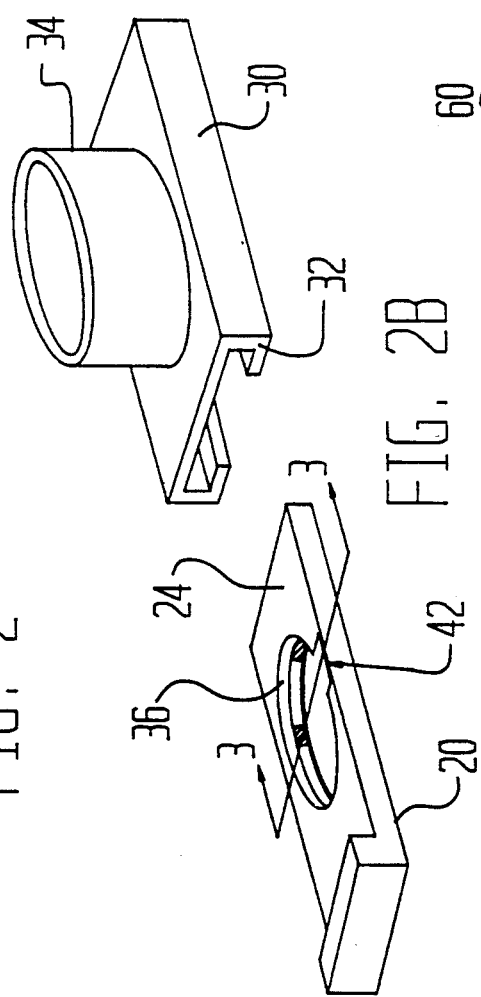

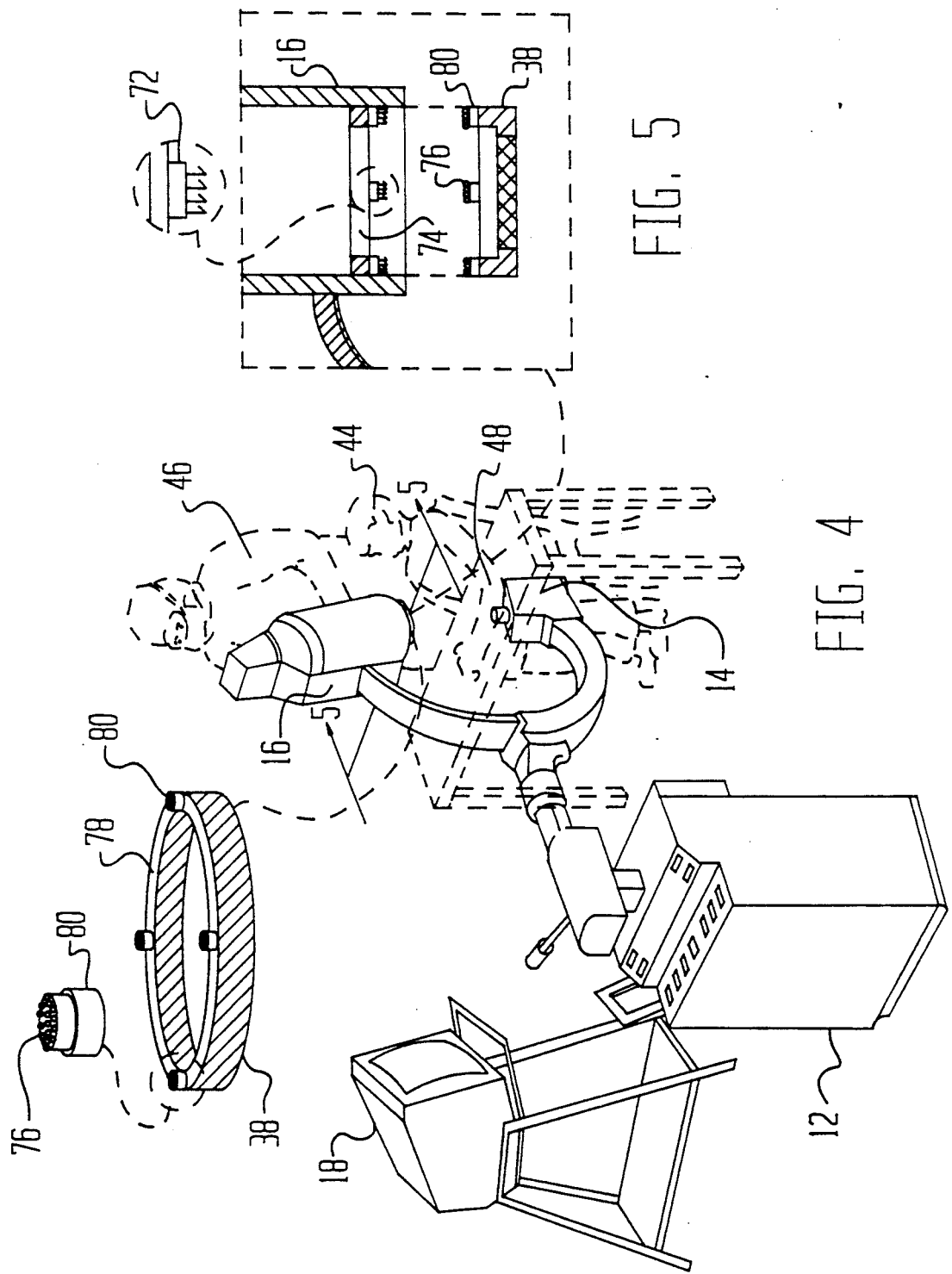

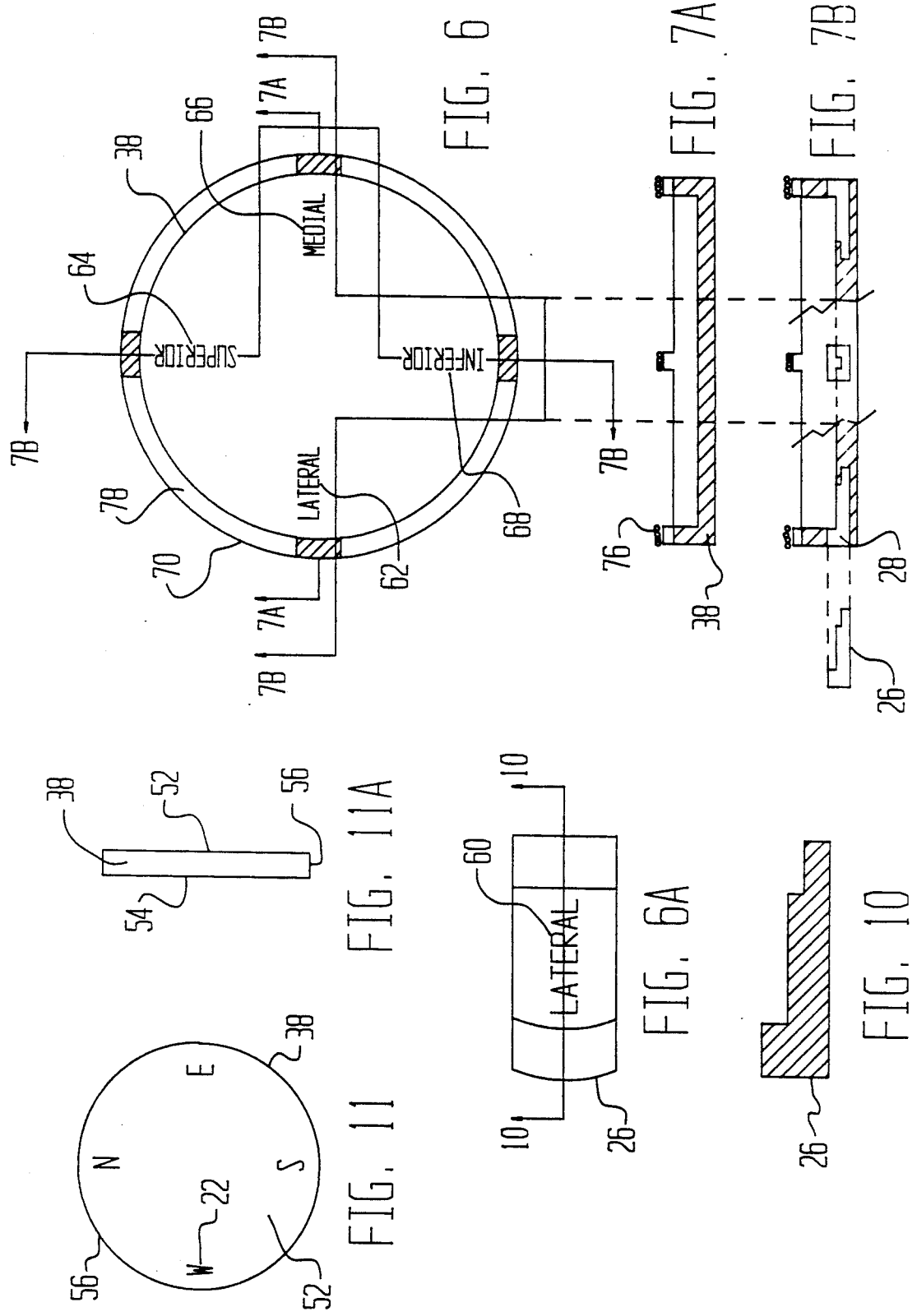

FLUOROSCOPY ORIENTATION DEVICE

BACKGROUND OF THE INVENTION

1. Field of the Invention

The present invention is directed to an orientation assistance device for use during image-intensified fluoroscopic examinations of internal structures and operations thereon. The invention is particularly useful in assisting medical personnel by eliminating disorientation during various medical procedures, accelerating the operation and thereby reducing the radiation exposure time.

2. Description of the Prior Art

One of the most routine x-ray examination procedures is fluoroscopy. The primary functions of the fluoroscope is to provide a visualization of the positioning of internal structures and motion of internal fluids, providing diagnostic information to the operator. Fluoroscopy is commonly used in engineering and related sciences, such as metallurgy, to examine structures, including searching for stress, wear, or flaws in various structures and components. Fluoroscopy is also used extensively in the medical field, supplying continuous information to physicians during medical procedures. It is similarly used in veterinary medicine.

Conventional fluoroscopy generates continuous images of internal structures on a fluoroscopic screen during a prolonged energization of the x-ray tube. With the recent introduction of new technological advances, including the application of computer technology to fluoroscopy and radiography, conventional fluoroscopy is quickly being replaced by image-intensified fluoroscopy. Image-intensified fluoroscopy uses a television monitor to display the image, yielding brighter fluoroscopic images than had previous conventional screens. The image-intensified fluoroscopic equipment is often referred to as a "C-arm," as the radiation source, the image-intensifying receiver and the apparatus connecting them is generally in the shape of a "C."

There are two ways of controlling the position of the C-arm during a fluoroscopic procedure; manually and by remote control. Most often, a technician controls the positioning of the C-arm with a remote control panel, centering the apparatus on the internal structure a physician will be operating upon. During medical procedures, a physician can make manual adjustments to the fluoroscope, such as targeting a new portion of a patient's body, changing the C-arm's tilt, and rotating the receiver tube. During medical procedures requiring sterile conditions, the remote control is used for making adjustments as the C-arm is enclosed in plastic. Generally, a technician operates the controls from an adjoining room as it becomes more awkward for the physician to move the plastic enshrouded device.

During medical procedures, the prolonged period of exposure to radiation necessary in fluoroscopic procedures, both to a patient and to medical personnel, has prompted research into methods of reducing the exposure time. Initially it was hoped that the use of image-intensified fluoroscopy, utilizing a television monitor to increase the brightness and resolution of the viewed image, would permit a tenfold reduction in the x-ray tube current, and thereby reduce the extent of exposure to the patient during a fluoroscopic procedure. However, the actual reduction has been far smaller. As a consequence, there has been no significant reduction in the patient's exposure to radiation, still considerably higher than from radiographic examinations.

The image produced on the monitor during a fluoroscopic examination provides no reference points to assist a doctor or technician in determining the orientation of the patient's internal structure. This forces either technicians or physicians to place something, either a radiopaque object or, often, their own hand, directly into the radiation field to help determine the true orientation of the observed body part. During complicated surgery, this can often be a very distracting and time consuming process for the surgeon. The lack of reference also hinders the technician in centering the fluoroscope over the injured area, slowing patient preparation and prolonging the radiation exposure to both the patient and staff members.

Alternative methods of reducing radiation exposure during fluoroscopy are being sought continually. During a medical fluoroscopic examination, the time spent by the technician generally falls in three areas: positioning the equipment and subject for proper irradiation, basically centering the apparatus on the desired area; examining the generated image for diagnostic purposes; and following the progress made by the physician as he operates on the patient, assisting the physician as necessary during the medical procedure. By minimizing the time expended in these three areas, exposure time is reduced for both the patient and technician.

U.S. Pat. No. 4,750,487, issued Jun. 14, 1988, to Zanetti, provides an apparatus used with fluoroscopy in guiding a needle to a target object within a body. U.S. Pat. No. 4,722,336, issued Feb. 2, 1988, to Kim et al., provides an apparatus used in conjunction with a fluoroscope to determining the precise three dimensional coordinates of an internal target, particularly in needle and drill placement for precise medical or surgical procedures, such as chemical injection, biopsy or orthopaedic procedures involving the bone, and a guide for positioning the penetrating instrument. Both of these inventions are useful in reducing exposure time, but only within the third stage of fluoroscopic use, during the medical procedure itself.

It is therefore the primary object of the invention to provide an orientation system which is easily employed by a fluoroscope operator during a fluoroscopic examination.

It is also an object of the present invention to provide a simple device that will allow radiologists or x-ray technicians to properly position a patient for examination during any medical fluoroscopic procedure.

A further object of the invention is to reduce the radiation exposure time to patients and medical staff during medical fluoroscopic procedures.

Another object of the present invention is to provide a device that will aid radiologists in orienting on the internal structure of a patient during fluoroscopic examinations without interfering or hindering the operation of the fluoroscope.

Yet another object of the present invention is to provide a device that can easily be secured to existing fluoroscopes without interfering in their normal operation.

It is a still further object of the present invention to provide an inexpensive device which is easily handled during use with an image-intensifying fluoroscope.

These and other objects of the present invention and the various features and details thereof are hereinafter set forth in the following detailed description of the invention.

SUMMARY OF THE INVENTION

In accordance with the present invention, an orientation device utilized in conjunction with an image-intensified fluoroscope for orienting on the internal structure displayed on the fluoroscope's monitor is disclosed, along with its method of use. The invention comprises: a radiolucent sheet; a radiopaque symbol or letter, or a series of the same, affixed to the disc; and means for securing the sheet to a fluoroscope's receiver, placing the sheet in the line of radiation between the subject and the receiver. The symbols or lettering on the sheet are clearly displayed on the monitor, indicating the true orientation of the internal structure being examined, aiding a fluoroscope's operator in adjusting the fluoroscope's position, and providing a fixed reference during any corrective procedures to be performed on the structure. The sheet may also be designed to receive an adjustable and interchangeable disc, wherein each disc contains the orientation symbols in a prearranged sequence.

The invention is particularly useful in reducing the length of exposure to radiation during medical procedures. The device provides guidance for a technician while preparing a patient and a clear reference for a physician to orient upon during a medical procedure, also allowing the technician to aid the attending physician during any procedure being performed.

An alternative embodiment, wherein the radiolucent sheet is disc-shaped and is fastened directly onto the receiver unit, preferably with hook and loop fasteners, is also disclosed.

BRIEF DESCRIPTION OF THE DRAWINGS

FIG. 1 is a perspective view of a C-arm fluoroscope unit with the present invention in place.

FIG. 1A is an exploded view of the present invention and the fluoroscope's receiver.

FIG. 2 is a top view of the sheet of the present invention.

FIG. 2A is a perspective view of the components of the present invention.

FIG. 2B is a perspective view of the an alternative embodiment of the present invention.

FIG. 3 is a side view of the present invention along line 3—3 of FIG. 2.

FIG. 4 is a perspective view of a C-arm fluoroscope unit showing the preferred embodiment of the present invention in the form of a disc.

FIG. 5 is a side view of a fluoroscopic receiver along line 5—5 of FIG. 4 illustrating one form of mounting means for the disc embodiment.

FIG. 6 is a top view of an alternative embodiment of the disc of the present invention showing alternative means for affixing orientation indicators.

FIG. 6A is a top view of an orientation insert used in the alternative embodiment of FIG. 6.

FIG. 7A is a side view of the present invention along line 7A—7A of FIG. 6.

FIG. 7B is a side view of the present invention along line 7B—7B of FIG. 6.

FIG. 10 is side view of the orientation insert along line 10—10 of FIG. 6A.

FIG. 11 is a top view of the disc of the present invention.

FIG. 11A is a side view of the disc of the present invention.

DETAILED DESCRIPTION OF THE DRAWINGS

Figure 9:
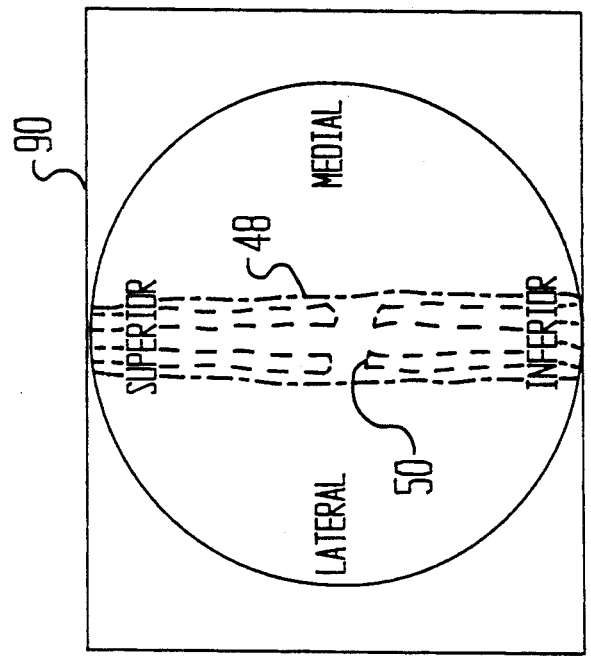
FIG. 9 is a front view of a television monitor of a C-arm image intensified fluoroscope unit with the present invention in place.

The present invention is described with reference to the enclosed Figures wherein the same numbers are used as applicable.

FIG. 1 illustrates the present invention 10 and an image-intensified fluoroscope 12. The fluoroscope 12 consists of: an x-ray radiation source 14; a receiver or image-intensifier tube 16; and a monitor 18, which can be either a mirror optics system or, preferably, a television monitor, the monitor 18 being operatively coupled to the receiver tube 16. The radiation source 14 and receiver 16 are connected by a C-shaped structure, resulting in the entire fluoroscope 12 being commonly referred to as a "C-arm."

FIG. 2 shows the present invention 10, a radiolucent sheet 20 incorporating orientation indicators, designed for use in conjunction with the fluoroscope 12 during any fluoroscopic procedure. The sheet 20 can be made from any material which is essentially transparent to x-ray radiation, such as glass or, preferably, plastic. Although the entire sheet 20 need not be radiolucent, an area at least as large as the receiver must be transparent to x-ray radiation or it may interfere with full use of the field of examination. The sheet 20 can be any thickness, with different advantages, such as flexibility, strength, durability, or rigidity, realized depending on the thickness used.

Radiopaque symbols 22 are affixed to the sheet 20, providing a point of reference on which an observer viewing the monitor 18 may orient. Although any symbols may be used in providing this point of reference, alphanumeric characters are generally recommended, as they can be combined to form words, phrases or abbreviations clearly discernable on the monitor 18 during a fluoroscopic procedure. The manner in which the fluoroscope 12 is to be utilized will dictate the type of symbol employed.

The sheet 20 may be manufactured with the radiopaque symbols 22 forming a permanent and integral part of the sheet 20. However, to permit greater flexibility in its use, the sheet 20 may be designed to include structural features which provide for the placement and replacement of the symbols 22, permitting the symbols 22 to be interchanged whenever desired. A variety of methods may be used to secure the symbols 22 to the radiolucent sheet 20 including, but not limited to: adhesives and other bonding agents, either permanent or temporary in duration, which can be applied to either the sheet 20 or the symbols 22 or both; hook and loop fasteners, (hereinafter referred to under the tradename VELCRO); and physical restraints integral to the sheet. The physical restraints may include: depressions in the surface 24; paired flanges forming slots at intervals along the surface designed to receive stencils bearing a radiopaque symbol 22, permitting an operator to create any combination of symbols 22 desired; or, as shown in FIGS. 6, 6A, and 7B, any of a number of tabs 26 bearing symbols 22 which can be inserted into slots 28 formed in the sides of the sheet 20. The tabs 26 may be manufactured or otherwise prepared in advance to bear the desired symbol 22 or sequence of symbols for any anticipated use of the present invention 10.

The sheet 20 is mounted so as to directly cover the receiver 16, placing the orientation symbols 22 between the receiver 16 and the object being examined. The sheet 20 should be moveable so as to allow an operator of the fluoroscope 12 to adjust its position and thereby provide an accurate system of orientation with the symbols 22 or words.

A mounting system for this embodiment is shown in FIGS. 1 and 2A, comprising a support tray 30 attached to a tray mount 34 and containing tray arms 32 for supporting the sheet 20 can be placed. The support tray aligns the orientation symbols 22 on the sheet 20 with the receiver 16. The sheet 20 can be held in place in a number of ways, including friction, VELCRO fasteners, adhesives, or any of a variety of fastening means such as clamps or clips. The tray 30 may be rotatably attached to the tray mount 34, permitting the operator to rotate the orientation symbols 22, holding the sheet 20 firmly as the tray 30 changes position. The tray mount 34 is secured to the receiver tube 16 prior to use. Although the tray mount may be permanently affixed to the receiver 16, securing means which permit removal of the tray mount 34 from the receiver 16 after use is preferred, such as clamping means.

An alternative embodiment of the sheet 20 is shown in FIG. 2B and comprises a cavity 36 in the sheet 20 designed to interchangeably hold a radiolucent disc 38 as shown in FIGS. 4, 11 and 11A. As shown in FIG. 3, the disc 38 is placed in the cavity 36 and held in place by a spacing insert 40 placed within a spacing grove 42 provided adjacent to the cavity 36. In this embodiment, the radiopaque symbols 22 are affixed to the disc 38, providing a point of reference for an observer viewing the monitor 18. The manner in which the symbols 22 are affixed are similar to those described before. The disc 38 may be interchanged with other discs as needed, the operator employing the appropriate disc required by each examination.

Figure 8:
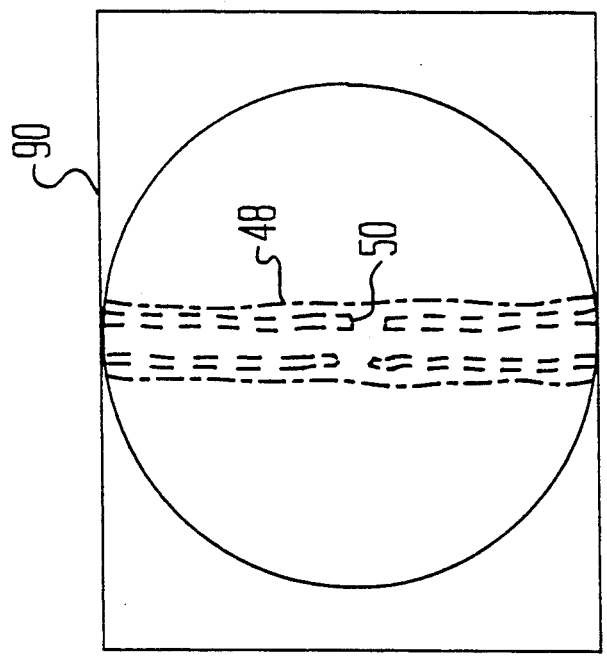
FIG. 8 is a front view of a television monitor of a C-arm image intensified fluoroscope unit without the present invention.

FIGS. 4 and 9 illustrate a patient 44 with a broken arm being examined by a physician 46, both shown in phantom. Typically there is an attending x-ray technician or radiologist (not shown) to operate the fluoroscope 12 and assist a physician 44 during any medical procedure involving a fluoroscope 12. As shown in FIGS. 8 and 9, the image-intensified fluoroscope 12 is centered on the patient,s arm 48, specifically the broken bone 50, and is displayed on the television monitor 18.

In its preferred embodiment, as shown in FIGS. 4, 5 and 6, the sheet 20 is a disc 38. The disc 38 has a front surface 52, facing the object being examined, and a rear surface 54, facing the receiver tube 16. The disc 38 may be designed to hold radiopaque symbols 22 at any position on either surface, although by positioning the symbols around the outer edge 56 of the disc, a greater portion of the disc 38 remains unobstructed. The operator of the fluoroscope 12 must determine which surface must be used so that the symbols 22 are projected on the monitor 18 without either horizontal or vertical inversion. In this way, the symbols 22 are easily discernable to both the operator and the physician 44. For the sake of clarity, it will be assumed in this discussion that the symbols 22 are to be affixed to the front surface 52 of the disc 38.

Although the disc 38 can be manufactured with specific radiopaque symbols 22 permanently attached to its front surface 52, it may also be designed to permit the symbols 22 to be interchanged whenever desired. For example, the symbols 22 can be manufactured with an adhesive strip or coating (not shown), preferably one which permits easy removal and reuse. Another alternative, illustrated in FIG. 6, is to provide the disc 38 with a slot 28 designed to receive a tab 26, each tab 26 containing a series of radiopaque symbols 22. In this way, the operator of the fluoroscope 12 can place any symbol 22 or series of symbols 22 in any desired slot 28, changing them as necessary for each fluoroscopic procedure. As noted above, it is preferred that the symbols be held at ninety degree intervals around the disc outer edge 56.

Although any character or figure can serve as an orienting symbol 22, a series of words 60 made up of alphanumeric characters may offer the greatest degree of information. For medical examinations, the words LATERAL 62, SUPERIOR 64, MEDIAL 66, and INFERIOR 68 should offer medical staff the greatest amount of assistance during any operation. To best utilize these words, as shown in FIGS. 2A and 6, the word MEDIAL 66 is positioned at the zero degree point on the disc 38. The word SUPERIOR 64 would then be placed at the ninety degree point, LATERAL 62 at the one hundred and eighty degree point, and INFERIOR 68 at the two hundred and seventy degree point. Similarly, other uses of a fluoroscope 12 will benefit from providing combinations of symbols 22 to form pertinent words to aid in guiding the operator of the fluoroscope 12 during any procedure.

The disc 38 is designed to be the same width as the receiver 16, facilitating mounting the disc 38 onto the receiver 16. By mounting the disc 38 on the receiver 16, the orientation symbols 22 are positioned between the irradiated patient 44, or other object being examined, and the image intensifying receiver 16. The disc 38 contains an elevated ridge 70 rising out of its outer edge 56 to improve the fit of the disc 38 onto the receiver 16.

Although the disc 38 may be permanently mounted onto the receiver 16, in its preferred embodiment hook and loop fasteners or VELCRO are used to secure the disc 38 to the receiver 16, providing means for the disc 38 to be removably mounted to the receiver 16. Alternative means for removably mounting the disc 38 are available, and may be used in lieu of VELCRO means. In using VELCRO on the present invention 10, either hook or loop material is attached to the disc 38, with the corresponding material secured to the receiver 16. As shown in FIGS. 4 and 5, the receiver 16 has series of fastener material swatches 72 around its face 74 at measured intervals. The corresponding loop material 76 is positioned along the surface of the disc's elevated ridge 78 at the same measured intervals. The loop material may be mounted onto posts 80 in order to facilitate the disc's 38 removal and attachment.

The use of the present invention is now described. As shown in FIGS. 1 and 4, the present invention 10 is secured to the receiver tube 16. The sheet 20 is held in place between the patient 10 and the receiver tube 16. The fluoroscope 12 is centered on the area of concern, in this case the patient arm 48. The technician observes the patient arm 48 in the monitor 18. By observing the symbols 22 on the monitor 18, the technician has a reference point by which he may orient on the patient's arm 48, permitting proper centering of the fluoroscope 12 over the appropriate section of the arm 48. The physician 46 operating on the patient 44 can now view the monitor screen 90 and begin setting the broken arm bone 50 shown in FIGS. 8 and 9.

FIG. 8 shows the view provided on the monitor screen 90 without the present invention 10 in place. It is difficult for the physician 46 from observing the monitor screen 90 to determine what is the true position of the patient's arm 48 and the broken bone 50 without sticking his own hand directly into the radiation field produced by the fluoroscope 12. As shown in FIG. 9, once the present invention is used, the words 60 provide clear indication as to the orientation of the patient 44, and allow the physician 46 to begin operating properly on the patient 44 with a minimum of exposure to the radiation.

While the above detailed description has explained this invention, it should be understood that further modification, uses and/or adaptations of the invention are possible following, in general, the principle of the invention and including such departures from the present disclosure as come within known or customary practice in the art to which the invention pertains, and as may be applied to the essential features hereinbefore set forth, and as fall within the broad scope and spirit of the invention a set forth in the foregoing disclosure and the following claims, as well as the appended drawings.

What is claimed is:

1. A device for assisting an operator of a fluoroscope in orienting said fluoroscope on an object during a fluoroscopic examination, said fluoroscope comprising a fluoroscopic x-ray emission tube, a receiver tube, and a monitor operatively coupled to said receiver tube for displaying a radiographic image of an internal structure of said object, which device comprises:
    a sheet transparent to x-ray radiation, said sheet possessing orientation indication means; and
    means for positioning said sheet between said object and said receiver tube, said positioning means being attached to said fluoroscope;
    wherein a surface of said x-ray transparent sheet contains a cavity for receiving an x-ray transparent disc and means for securing said disc in said cavity, said disc possessing said orientation indication means.

2. The device of claim 1 wherein said orientation indication means are radiopaque symbols affixed to said sheet.

3. The device of claim 2 wherein said radiopaque symbols are removably secured to said sheet.

4. The device of claim 2 wherein said radiopaque symbols are alphanumeric characters which may be combined to form a variety of messages.

5. The device of claim 1 wherein said orientation indication means includes: a radiolucent tab; a slot in a side of said disc for receiving said radiolucent tab; and radiopaque symbols affixed to said tab.

6. The device of claim 1 wherein said means for positioning said sheet comprises an adjustable mount integrally connected to said receiver tube for holding and securing said x-ray transparent sheet and for permitting accurate positioning of said sheet during said examination.

7. The device of claim 1 wherein said means for positioning said sheet comprises means to removably secure said x-ray transparent sheet to said receiver tube, said means being integral with said receiver tube.

8. The device of claim 7 wherein said means to removably secure said sheet comprises hook and loop fasteners.

9. The device of claim 1 wherein the x-ray transparent sheet is a disc, said disc having an outer circumferential edge.

10. The device of claim 9 wherein said means for positioning said sheet comprises hook and loop fasteners integral with said receiver tube and said outer circumferential edge of said disc.

11. The device of claim 5 wherein said orientation means includes locking means for holding said tab in said slot.

12. A device for assisting in orienting a fluoroscope on an object during fluoroscopic examination, said fluoroscope comprising a fluoroscopic x-ray emission tube, a receiver tube, and a monitor operatively coupled to said receiver tube, for displaying a radiographic image of the internal structure of said object, which device comprises:
    an x-ray radiation transparent disc with a circumferential outer edge;
    radiopaque symbols;
    means for securing said symbols to said disc, thereby indicating an orientation; and
    means for removably attaching said disc to said receiver tube, said attaching means positioning said disc between said object and said receiver tube so as to permit said orientation symbols to be perceived on said monitor during operation of said fluoroscope;
    wherein said means for securing said symbols to said disc comprises a radiolucent tab; a slot in a side of said sheet for securing said radiolucent tab; and radiopaque symbols affixed to said tab.

13. The device of claim 12 wherein said symbols are alphanumeric characters which may be combined to form a variety of messages.

14. The device of claim 13 wherein said alphanumeric characters spell the words "medial," "lateral," "superior," and "inferior" along said outer edge of said disc, where "medial" is affixed at a 0 degree point, "superior" is affixed to said disc at a 90 degree point, "lateral" is affixed at a 180 degree mark, and "inferior" is affixed at a 270 degree mark.

15. The device of claim 12 wherein said attaching means comprises an adjustable mount integrally connected to said receiver tube for holding and securing said disc and permitting accurate positioning of said disc during said examination.

16. The device of claim 15 wherein said attaching means further permits for axial rotation of said disc relative to said image-intensifying tube.

17. The device of claim 16 wherein said attaching means comprises hook and loop fasteners.

18. The device of claim 12 wherein said means for securing said symbols to said disc includes locking means for holding said tab in said slot.

19. A device for assisting in orienting a fluoroscope on an object during a fluoroscopic examination, said fluoroscope comprising a fluoroscopic x-ray emission tube, a receiver tube, and a monitor operatively coupled to said receiver tube, for displaying a radiographic image of the internal structure of said object, which device comprises:
    an x-ray radiation transparent sheet, including a cavity and an x-ray radiation transparent disc adapted to be secured within said cavity;
    radiopaque symbols affixed to said disc indicating orientation;

means for attaching said sheet to said receiver tube, said attaching means positioning said sheet between said object and said receiver tube so as to permit said orientation symbols to be perceived on said monitor during operation of said fluoroscope.

20. The device of claim 19 wherein means are provided for removably affixing said symbols to said disc, which means comprises: a radiolucent tab; a slot in a side of said disc for securing said radiolucent tab; and radiopaque symbols affixed to said tab.

* * * * *